(12) United States Patent
Keith

(10) Patent No.: US 7,846,930 B2
(45) Date of Patent: Dec. 7, 2010

(54) DIARYL-SUBSTITUTED TETRAHYDROISOQUINOLINES AS HISTAMINE H₃ RECEPTOR AND SEROTONIN TRANSPORTER MODULATORS

(75) Inventor: John M. Keith, San Diego, CA (US)

(73) Assignee: Janssen Pharmaceutica NV (BE)

( * ) Notice: Subject to any disclaimer, the term of this patent is extended or adjusted under 35 U.S.C. 154(b) by 297 days.

(21) Appl. No.: 12/119,811

(22) Filed: May 13, 2008

(65) Prior Publication Data

US 2008/0318952 A1    Dec. 25, 2008

Related U.S. Application Data

(60) Provisional application No. 60/938,790, filed on May 18, 2007.

(51) Int. Cl.
| | |
|---|---|
| A61K 31/5377 | (2006.01) |
| A61K 31/4725 | (2006.01) |
| C07D 217/14 | (2006.01) |
| C07D 413/14 | (2006.01) |
| C07D 413/12 | (2006.01) |

(52) U.S. Cl. .................... 514/235.2; 514/307; 546/150; 544/128

(58) Field of Classification Search ................ 546/150; 544/128; 514/307, 235.2
See application file for complete search history.

(56) References Cited

U.S. PATENT DOCUMENTS

| 4,113,869 A | 9/1978 | Gardner et al. |
| 2006/0194837 A1 | 8/2006 | Carruthers et al. |
| 2006/0287292 A1 | 12/2006 | Carruthers et al. |
| 2006/0293316 A1 | 12/2006 | Apodaca et al. |

FOREIGN PATENT DOCUMENTS

| WO | WO 01/32624 A | 5/2001 |
| WO | WO 2006/066197 A | 6/2006 |

OTHER PUBLICATIONS

Bagshawe, K.D.: "Antibody-Directed Enzyme Prodrug Therapy: A Review"; Drug Devel. Research (1995) 34: 220-230.
Barbier, A.J. et al.: Acute wake-promoting actions of JNJ-5207852, a novel, diamine-based H3 antagonist; British J. of Pharmacology (2004) 143: 649-661.
Barnes, J.C. et al.: The Selective Histamine H3 Receptor Antagonist thioperamide Improves Cognition and Enhances Hippocampal Acetylcholine Release in Vivo. Soc. Neurosci. Abstr. (1993) 19: 1813.
Beasley, C.M., Jr., MD, et al.: "Adverse Events and Treatment Discontinuations in Clinical Trials of Fluoxetine in Major Depressive Disorder: An Updated Meta-Analysis"; Clinical Therapeutics (2000) 22(11): 1319-1330.
Berge, S.M. et al.: "Pharmaceutical Salts"; J. of Pharmaceutical Sciences (1977) 66(1): 1-19.
Bertolini, G. et al.: "A New Rational Hypothesis for the Pharmacophore of the Active Metabolite of Leflunomide, A Potent Immunosuppressive Drug"; J. Med. Chem. (1997) 40: 2011-2016.
Bodor, N.: Novel Approaches to the Design of Safer Drugs: Soft Drugs and Site-Specific Chemical Delivery Systems; Advances in Drug Research (1984) 13: 255-331.
Chen, Z.: "Effect of histamine $H_3$-receptor antagonst clobenpropit on spatial memory of radial maze performance in rats"; Acta Pharmacol Sin (2000) 21(10): 905-910.
Fava, G.A. et al.: "Residual symptoms in depression: An emerging therapeutic target"; Prog. Neruo-Psychopharmacology & Biol. Psychiatry (2002) 26(6): 1019-1027.
Fleisher, D. et al.: "Improved oral drug delivery: solubility limitations overcome by the use of prodrugs"; Adv. Drug Del. Rev. (1996) 19: 115-130.
Fox, G.B. et al.: "Effects of histamine $H_3$ receptor ligands GT-2331 and ciproxifan in a repeated acquisition avoidance response in the spontaneously hypertensive rat pup"; Behavioural Brain Research (2002) 131: 151-161.
Hill, S.J. et al.: "International Union of Pharmacology. XIII. Classification of Histamine Receptors"; Pharmacol. Rev. (1997) 49(3): 253-278.
Jané-Lopis, E. et al.: "Predictors of efficacy in depression prevention programmes"; Br. J. Psychiatry (2003) 183: 384-397.
Keith, J.M. et al.: "Dual serotonin transporter inhibitor/histamine H3 antagonists: Development of rigidified H3 pharmacophores"; Bioorg. & Med. Chem. Letters (2007) 17(19): 5325-5329.
Lamberti, C. et al.: "Antidepressant-like effects of endogenous histamine and of two histamine $H_1$ receptor agonists in the mouse forced swim test"; British J. of Pharmacology (1998) 123(7): 1331-1336.
Leurs, R. et al.: The Medicinal Chemistry and Therapeutic Potentials of Ligands of the Histamine H3 Receptor; Prog. Drug. Res. (1995) 45: 107-165.
Lintunen et al.: "Increased brain histamine in an alcohol-preferring rat line and modulation of ethanol consumption by $H_3$ receptor mechanisms[1]"; FASEB Journal (2001) 15(6): 1074-1076.
Machidori, H. et al.: Zucker Obese Rats: Defect in Brain Histamine Control of Feeding; Brain Res. (1992) 590: 180-186.
Miyazaki, S. et al.: "Effects of Thioperamide on the Cholinergic System and the Step-Through Passive Avoidance Test in Mice"; Meth Find Exp Clin Pharmacol (1995) 17(10): 653-658.
Miyazaki, S. et al.: "Effects of Thioperamide, a Histamine $H_3$-receptor Antagonist, on a Scopolamine-induced Learning Deficit Using an Elevated Plus-maze Test in Mice"; Life Sciences, (1995) 57(23): 2137-2144.
Monti, J.M. et al.: "Effects of selective activation or blockade of the histamine H3receptor on sleep and wakefulness"; Eur. J. of Pharmacology (1991) 205: 283-287.
Morisset, S. et al.: High Constitutive Activity of Native H3 Receptors Regulates Histamine Neurons in Brain. Nature (Dec. 2000) 408: 860-864.

(Continued)

*Primary Examiner*—Rebecca L Anderson
(74) *Attorney, Agent, or Firm*—Michael J. Atkins

(57) ABSTRACT

Certain diaryl-substituted tetrahydroisoquinoline compounds are histamine $H_3$ receptor and/or serotonin transporter modulators useful in the treatment of histamine $H_3$ receptor- and/or serotonin-mediated diseases.

15 Claims, No Drawings

OTHER PUBLICATIONS

Nierenberg, A.A., MD et al.: "Residual Symptoms in Depressed Patients Who Respond Acutely to Fluoxetine"; J. Clin. Psychiatry (Apr. 1999) 60: 221-225.

Orsetti, M. et al.: "Histamine $H_3$-receptor antagonism improves memory retention and reverses the cognitive deficit induced by scopolamine in a two-trial place recognition task"; Elsevier Behavioural Brain Research (2001) 124(2): 235-242.

Panula, P. et al.: Significant Changes in the Human Brain Histaminergic System in Alzheimer's Disease. Soc. Neurosci. Abstr. (1995) 21: 1977.

Perez-Garcia, C. et al.: "Effects of histamine $H_3$ receptor ligands in experimental models of anxiety and depression"; Psychopharmacology (1999) 142(2): 215-220.

Robinson, R.P. et al.: "Discovery of the Hemifumarate and (α-L-Alanyloxy)methyl Ether as Prodrugs of an Antirheumatic Oxindole: Prodrugs for the Enolic OH Group"; J. Med. Chem. (1996) 39: 10-18.

Schlicker, E. et al.: The Moderate Affinity of Clozapine at H3 Receptors Is Not Shared by Its Two Major Metabolites and by Structurally Related and Unrelated Atypical Neuroleptics. Naunyn-Schmiedeberg's Arch. Pharmacol. (1996) 353: 290-294.

Shan, D. et al.: "Prodrug Strategies Based on Intramolecular Cyclization Reactions"; J. of Pharm. Sciences (Jul. 1997) 86(7): 765-767.

Stark, H. et al.: Developments of Histamine H3-Receptor Antagonists. Drugs Future (1996) 21(5): 507-520.

Yokoyama, H. et al.: Effect of Thioperamide, a Histamine $H_3$ Receptor Antagonist, on Electrically Induced Convulsions in Mice. Eur. J. Pharmacol. (1993) 234: 129-133.

Zajecka, J.M., MD: "Clinical Issues in Long-Term Treatment With Antidepressants"; J. Clin. Psychiatry (2000) 61 (Suppl. 2): 20-25.

Bundgaard et al Design of Prodrugs Ed H Bundgaard Elsevier 1985.

Larsen et al Design and Application of Prodrugs Drug Design and Development Krogsgaard-Larsen et al Eds Harswood Academic Publishers 1991.

Leurs et al The Histamine H3 Receptor—A Target for New Drugs Leurs r. and Timmernam H. Eds Elsevier 1998.

Stahl et al Handbook of Pharmaceutical Salts, Properties Selection and Use Stahl and Wermuth Eds Wiley-VCH and VHCA Zurich 2002.

Barbier, et al. "Pharmacological Characterization of JNJ-28583867, A Histamine H3 Receptor Antagonist and Serotonin Reuptake Inhibitor". European Journal of Pharmacology, Amsterdam, NL., vol. 576, No. 1-3, Oct. 19, 2007, pp. 43-54.

PCT International Search Report for PCT/US2008/063516 dated Sep. 2, 2008.

DIARYL-SUBSTITUTED TETRAHYDROISOQUINOLINES AS HISTAMINE H$_3$ RECEPTOR AND SEROTONIN TRANSPORTER MODULATORS

CROSS-REFERENCE TO RELATED APPLICATIONS

This application claims the benefit of U.S. Provisional Application 60/938,790, filed May 18, 2007, which is hereby incorporated by reference in its entirety.

FIELD OF THE INVENTION

The present invention relates to certain substituted diaryl-substituted tetrahydroisoquinoline compounds, pharmaceutical compositions containing them, and methods of using them for the treatment of disease states, disorders, and conditions mediated by histamine H$_3$ receptor and/or serotonin transporter activity.

BACKGROUND OF THE INVENTION

The histamine H$_3$ receptor is primarily expressed in the mammalian central nervous system (CNS), with some minimal expression in peripheral tissues such as vascular smooth muscle. Several indications for histamine H$_3$ antagonists and inverse agonists have been proposed based on animal pharmacology and other experiments with known histamine H$_3$ antagonists (e.g. thioperamide). (See: "The Histamine H$_3$ Receptor-A Target for New Drugs", Leurs, R. and Timmerman, H., (Eds.), Elsevier, 1998; Morisset, S. et al., *Nature* 2000, 408, 860-864.) These include conditions such as cognitive disorders, sleep disorders, psychiatric disorders, and other disorders.

Compounds that possess histamine H$_3$ receptor activity and serotonin transporter (SERT) activity may be useful in the treatment of SERT-mediated disorders such as substance abuse disorders and sexual dysfunction (including premature ejaculation), and particularly beneficial in the treatment of depression. Activation of the H$_3$ receptor on neurons by histamine or an agonist decreases the release of several neurotransmitters including noradrenaline and serotonin, key neurotransmitters involved in depression (Hill, S. J. et al. *Pharmacol. Rev.* 1997, 49(3), 253-278). Although H$_3$ receptor antagonists alone may not be capable of increasing serotonin levels in vivo to those required for antidepressant effects, concomitant blockade of the SERT will simultaneously decrease the neuronal reuptake of these neurotransmitter molecules, leading to enhanced concentrations of serotonin in the synaptic cleft and an enhanced therapeutic effect and a potentially reduced side effect profile as compared to a compound with SERT activity alone.

Histamine H$_3$ antagonists have been shown to have pharmacological activity relevant to several key symptoms of depression, including sleep disorders (e.g. sleep disturbances, fatigue, and lethargy) and cognitive difficulties (e.g. memory and concentration impairment), as described above. Therefore, a combined H$_3$/SERT modulating compound would provide symptomatic relief for the sleep disorders, fatigue, and cognitive problems during the first weeks of treatment, before the mood-elevating effect of the SERT modulation is noticed.

Fatigue is a frequent symptom experienced by the more than 340 million people worldwide who are suffering from depression (Jane-Llopis, E.; Hosman, C.; Jenkins, R.; Anderson, P. *Br. J. Psychiatry; J. Mental Sci.*, 2003, 183, 384-397). While antidepressants, particularly selective serotonin reuptake inhibitors (SSRIs), are frequently able to improve the overall sense of wellbeing for those who use them, these drugs often fail to improve the symptom of fatigue even as mood improves (Nierenberg, A. A.; Keefe, B. R.; Leslie, V. C.; Alpert, J. E.; Pava, J. A.; Worthington, J. J. 3rd; Rosenbaum, J. F.; Fava, M. *J. Clin. Psychiatry*, 1999, 60, 221-225; Fava, G. A.; Fabbri, S.; Sonino, N. *Prog. Neuro-Psychopharmacol. Biol. Psych.* 2002, 26, 1019-1027). Some SSRIs even induce fatigue and excessive sleepiness (Beasley, C. M., Jr.; Koke, S. C.; Nilsson, M. E.; Gonzales, J. S. *Clin. Ther.* 2000, 22, 1319-1330; Zajecka, J. M. *J. Clin. Psychiatry*, 61 Suppl 2 2000, 20-25).

One possible approach to mitigating the fatigue associated with depression and/or its treatment is through the use of a wake promoting agent. Histamine H$_3$ receptor antagonists are known to increase wakefulness (Monti, J. M.; Jantos, H.; Boussard, M.; Altier, H.; Orellana, C.; Olivera, S. *Eur. J. Pharmacol.* 1991, 205, 283-287) without showing nonspecific stimulant effects such as increased locomotor activity (Barbier, A. J.; Berridge, C.; Dugovic, C.; Laposky, A. D.; Wilson, S. J.; Boggs, J.; Aluisio, L.; Lord, B.; Mazur, C.; Pudiak, C. M.; Langlois, X.; Xiao, W.; Apodaca, R.; Carruthers, N. I.; Lovenberg, T. W. *Br. J. Pharmacol.* 2004, 143, 649-661). Thus the case can be made that H$_3$ antagonists would be useful adjuncts to antidepressant therapy.

As part of our strategy for the development of novel approaches to the treatment of depression, we have investigated the possibility of combining histamine H3 antagonism with serotonin transporter (SERT) inhibition in a single chemical entity.

We have recently described several chemical series with high affinities for both targets. Such compounds having H$_3$ receptor activity and SERT activity have been disclosed in U.S. Patent Appl. Publ. Nos. US 2006/0194837 (Aug. 31, 2006), US 2006/0293316 (Dec. 28, 2006), and US 2006/0287292 (Dec. 21, 2006), which are each hereby incorporated by reference. Compounds described herein were discussed by Keith et al. (Bioorg. Med. Chem. Lett. 2007, 17(19), 5325-5329).

However, there remains a need for potent histamine H$_3$ receptor and/or serotonin transporter modulators with desirable pharmaceutical properties. Herein is described the effect of replacing the flexible propyloxypiperidine side chain with a more rigid and polar aromatic spacer.

SUMMARY OF THE INVENTION

Certain diaryl-substituted tetrahydroisoquinoline derivatives have now been found to have histamine H$_3$ receptor and/or serotonin transporter modulating activity. Thus, the invention is directed to the general and preferred embodiments defined, respectively, by the independent and dependent claims appended hereto, which are incorporated by reference herein.

In one general aspect the invention relates to a compound of the following Formula (I):

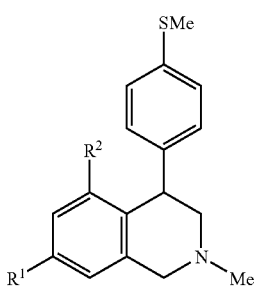

wherein
one of R¹ and R² is H and the other is

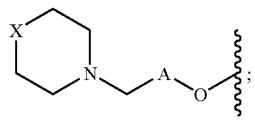

where A is phenyl, pyridyl, or thiazolyl; and
X is CH₂, O, or CHF;

or a pharmaceutically acceptable salt, pharmaceutically acceptable prodrug, or pharmaceutically active metabolite of such compound.

In a further general aspect, the invention relates to pharmaceutical compositions each comprising: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

In another general aspect, the invention is directed to a method of treating a subject suffering from or diagnosed with a disease, disorder, or medical condition mediated by histamine $H_3$ receptor and/or serotonin transporter activity, comprising administering to the subject in need of such treatment an effective amount of a compound of Formula (I), or a pharmaceutically acceptable salt, pharmaceutically acceptable prodrug, or pharmaceutically active metabolite thereof.

In certain preferred embodiments of the inventive method, the disease, disorder, or medical condition is selected from: cognitive disorders, sleep disorders, psychiatric disorders, and other disorders.

Additional embodiments, features, and advantages of the invention will be apparent from the following detailed description and through practice of the invention.

DETAILED DESCRIPTION OF INVENTION AND ITS PREFERRED EMBODIMENTS

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by a/symbol), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

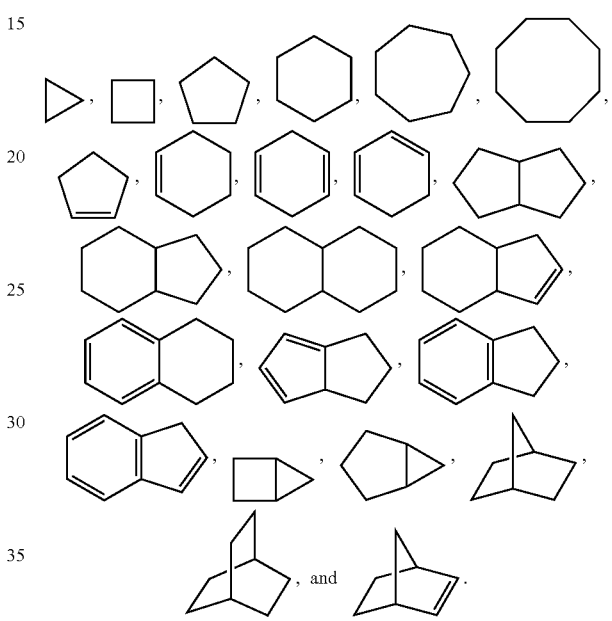

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

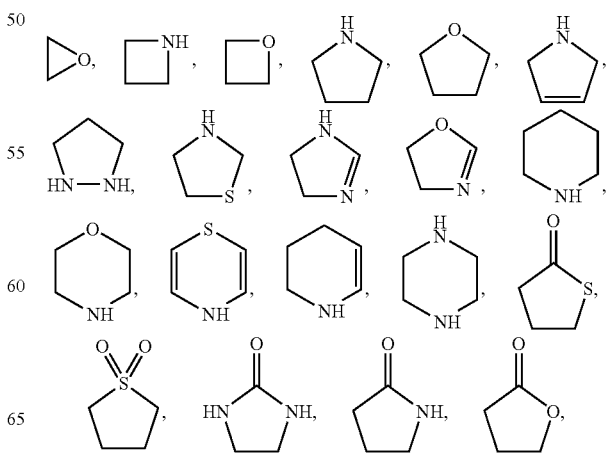

-continued

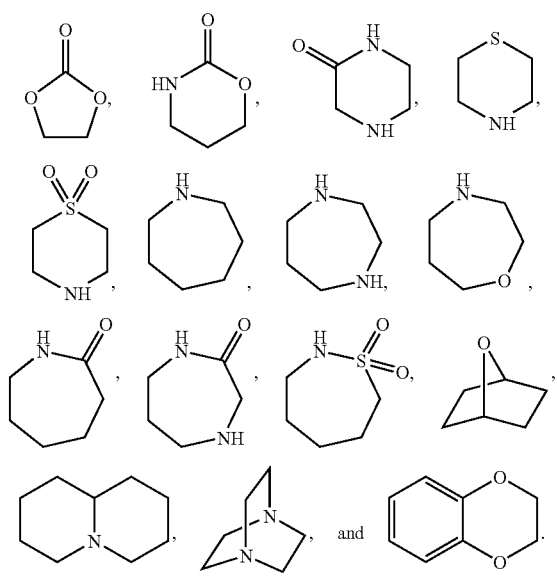

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

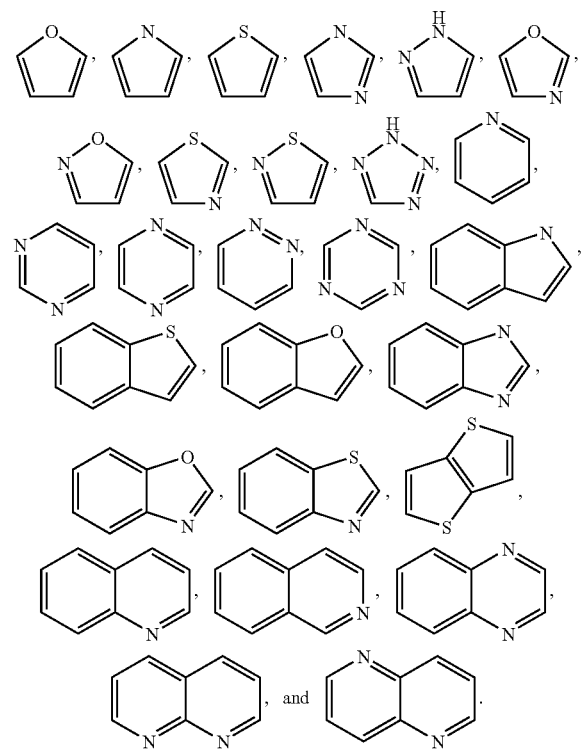

Those skilled in the art will recognize that the species of heteroaryl, cycloalkyl, and heterocycloalkyl groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}O$, $^{17}O$, $^{32}P$, $^{33}P$, $^{35}S$, $^{18}F$, $^{36}Cl$, and $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of Formula (I), R¹ is

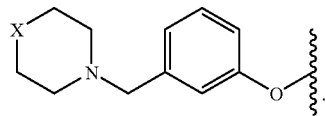

In further preferred embodiments, R¹ is

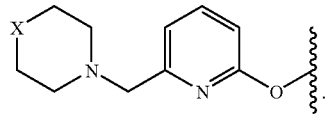

In still further preferred embodiments, R¹ is

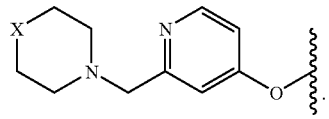

In still further preferred embodiments, R¹ is

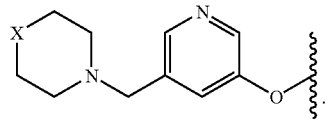

In still further preferred embodiments, R¹ is

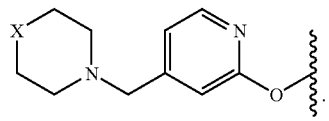

In still further preferred embodiments, R¹ is

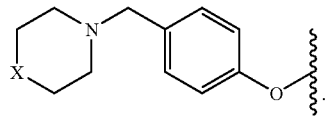

In still further preferred embodiments, R¹ is

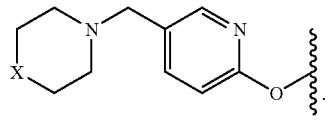

In still further preferred embodiments, R¹ is

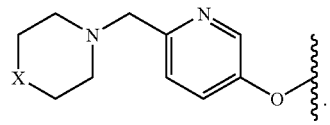

In still further preferred embodiments, R¹ is

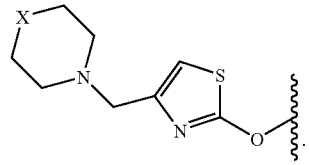

In still further preferred embodiments, R¹ is

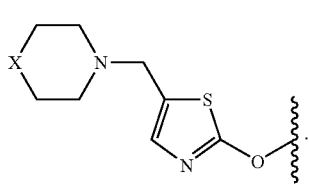

In certain preferred embodiments, the compound of Formula (I) is selected from the group consisting of: 2-Methyl-4-(4-methylsulfanyl-phenyl)-7-(3-piperidin-1-ylmethyl-phenoxy)-1,2,3,4-tetrahydro-isoquinoline; 2-Methyl-4-(4-methylsulfanyl-phenyl)-5-(3-piperidin-1-ylmethyl-phenoxy)-1,2,3,4-tetrahydro-isoquinoline; 2-Methyl-4-(4-methylsulfanyl-phenyl)-7-(6-piperidin-1-ylmethyl-pyridin-2-yloxy)-1,2,3,4-tetrahydro-isoquinoline; 2-2-Methyl-4-(4-methylsulfanyl-phenyl)-7-(2-piperidin-1-ylmethyl-pyridin-4-yloxy)-1,2,3,4-tetrahydro-isoquinoline; 2-Methyl-4-(4-methylsulfanyl-phenyl)-5-(2-piperidin-1-ylmethyl-pyridin-4-yloxy)-1,2,3,4-tetrahydro-isoquinoline; 2-Methyl-4-(4-methylsulfanyl-phenyl)-7-(5-piperidin-1-ylmethyl-pyridin-3-yloxy)-1,2,3,4-tetrahydro-isoquinoline; 2-Methyl-4-(4-methylsulfanyl-phenyl)-5-(5-piperidin-1-ylmethyl-pyridin-3-yloxy)-1,2,3,4-tetrahydro-isoquinoline; 2-Methyl-4-(4-methylsulfanyl-phenyl)-7-(4-piperidin-1-ylmethyl-pyridin-2-yloxy)-1,2,3,4-tetrahydro-isoquinoline; 2-Methyl-4-(4-methylsulfanyl-phenyl)-7-(4-piperidin-1-ylmethyl-thiazol-2-yloxy)-1,2,3,4-tetrahydro-isoquinoline; 2-Methyl-4-(4-methylsulfanyl-phenyl)-7-(5-piperidin-1-ylmethyl-pyridin-2-yloxy)-1,2,3,4-tetrahydro-isoquinoline; 2-Methyl-4-(4-methylsulfanyl-phenyl)-7-(6-piperidin-1-ylmethyl-pyridin-3-yloxy)-1,2,3,4-tetrahydro-isoquinoline; 2-Methyl-4-(4-methylsulfanyl-phenyl)-7-(4-piperidin-1-ylmethyl-phenoxy)-1,2,3,4-tetrahydro-isoquinoline; 2-Methyl-4-(4-methylsulfanyl-phenyl)-7-(5-morpholin-4-ylmethyl-pyridin-2-yloxy)-1,2,3,4-tetrahydro-isoquinoline; 2-Methyl-4-(4-methylsulfanyl-phenyl)-7-(4-morpholin-4-ylmethyl-thiazol-2-yloxy)-1,2,3,4-tetrahydro-isoquinoline; 7-[5-(4-Fluoro-piperidin-1-ylmethyl)-pyridin-2-yloxy]-2-methyl-4-(4-methylsulfanyl-phenyl)-1,2,3,4-tetrahydro-isoquinoline; 2-Methyl-4-(4-methylsulfanyl-phenyl)-7-(5-piperidin-1-yl-methyl-thiazol-2-yloxy)-1,2,3,4-tetrahydro-isoquinoline;

and pharmaceutically acceptable salts thereof.

The invention includes also pharmaceutically acceptable salts of the compounds represented by Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, ☐yridine, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al. *J. Med. Chem.* 1997, 40, 2011-2016; Shan, et al. *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of the histamine $H_3$ receptor and/or the serotonin transporter in the methods of the invention. Accordingly, the invention relates to methods of using the compounds of the invention to treat subjects diagnosed with or suffering from a disease, disorder, or condition mediated by histamine $H_3$ receptor and/or serotonin transporter activity, such as those described herein.

The term "treat" or "treating" as used herein is intended to refer to administration of a compound or composition of the invention to a subject for the purpose of effecting a therapeutic or prophylactic benefit through modulation of histamine $H_3$ receptor and/or the serotonin transporter activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_3$ receptor and/or the serotonin transporter activity. The term "subject" refers to a mammalian patient in need of such treatment, such as a human. "Modulators" include both inhibitors and activators, where "inhibitors" refer to compounds that decrease, prevent, inactivate, desensitize or down-regulate histamine $H_3$ receptor and/or the serotonin transporter expression or activity, and "activators" are compounds that increase, activate, facilitate, sensitize, or up-regulate histamine $H_3$ receptor and/or the serotonin transporter expression or activity.

Accordingly, the invention relates to methods of using the compounds described herein to treat subjects diagnosed with or suffering from a disease, disorder, or condition mediated by histamine $H_3$ receptor and/or the serotonin transporter activity, such as: cognitive disorders, sleep disorders, psychiatric disorders, and other disorders. Symptoms or disease states are intended to be included within the scope of "medical conditions, disorders, or diseases."

Cognitive disorders include, for example, dementia, Alzheimer's disease (Panula, P. et al., *Soc. Neurosci. Abstr.* 1995, 21, 1977), cognitive dysfunction, mild cognitive impairment (pre-dementia), attention deficit hyperactivity disorders (ADHD), attention-deficit disorders, and learning and memory disorders (Barnes, J. C. et al., *Soc. Neurosci. Abstr.* 1993, 19, 1813). Learning and memory disorders include, for example, learning impairment, memory impairment, age-related cognitive decline, and memory loss. $H_3$ antagonists have been shown to improve memory in a variety of memory tests, including the elevated plus maze in mice (Miyazaki, S. et al. *Life Sci.* 1995, 57(23), 2137-2144), a two-trial place recognition task (Orsetti, M. et al. *Behav. Brain Res.* 2001, 124(2), 235-242), the passive avoidance test in mice (Miyazaki, S. et al. *Meth. Find. Exp. Clin. Pharmacol.* 1995, 17(10), 653-658) and the radial maze in rats (Chen, Z. *Acta Pharmacol. Sin.* 2000, 21(10), 905-910). Also, in the spontaneously hypertensive rat, an animal model for the learning impairments in attention-deficit disorders, $H_3$ antagonists were shown to improve memory (Fox, G. B. et al. *Behav. Brain Res.* 2002, 131(1-2), 151-161).

Sleep disorders include, for example, insomnia, disturbed sleep, narcolepsy (with or without associated cataplexy), cataplexy, disorders of sleep/wake homeostasis, idiopathic somnolence, excessive daytime sleepiness (EDS), circadian rhythm disorders, fatigue, lethargy, jet lag, and REM-behavioral disorder. Fatigue and/or sleep impairment may be caused by or associated with various sources, such as, for example, sleep apnea, perimenopausal hormonal shifts, Parkinson's disease, multiple sclerosis (MS), depression, chemotherapy, or shift work schedules.

Psychiatric disorders include, for example, schizophrenia (Schlicker, E. and Marr, I., *Naunyn-Schmiedeberg's Arch. Pharmacol.* 1996, 353, 290-294), bipolar disorders, manic disorders, depression (Lamberti, C. et al. *Br. J. Pharmacol.* 1998, 123(7), 1331-1336; Perez-Garcia, C. et al. Psychopharmacology 1999, 142(2), 215-220) (Also see: Stark, H. et al., *Drugs Future* 1996, 21(5), 507-520; and Leurs, R. et al., *Prog. Drug Res.* 1995, 45, 107-165 and references cited therein.), obsessive-compulsive disorder, and post-traumatic stress disorder.

Other disorders include, for example, motion sickness, vertigo (e.g. vertigo or benign postural vertigo), tinitus, epilepsy (Yokoyama, H. et al., *Eur. J. Pharmacol.* 1993, 234, 129-133), migraine, neurogenic inflammation, neuropathic pain, Down Syndrome, seizures, eating disorders (Machidori, H. et al., *Brain Res.* 1992, 590, 180-186), obesity, substance abuse disorders, movement disorders (e.g. restless legs syndrome), eye-related disorders (e.g. macular degeneration and retinitis pigmentosis), and drug addiction (including alcoholism; See: Lintunen et al. *FASEB J.* 2001, 15, 1074-1076).

Particularly, as modulators of the histamine $H_3$ receptor and/or the serotonin transporter, the compounds of the present invention are useful in the treatment or prevention of depression, disturbed sleep, narcolepsy, fatigue, lethargy, cognitive impairment, memory impairment, memory loss, learning impairment, attention-deficit disorders, and eating disorders.

In a treatment method according to the invention, an effective amount of a compound according to the invention is administered to a subject suffering from or diagnosed as having such a disease, disorder, or condition. An "effective amount" means an amount or dose sufficient to generally bring about the desired therapeutic or prophylactic benefit in patients in need of such treatment.

Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.001 to 100 mg/kg/day, or about 0.001 to 35 mg/kg/day, in single or divided dosage units (e.g., BID, TID, QID). For a 70-kg human, an illustrative range for a suitable dosage amount is from about 0.05 to about 70 mg/day, or about 1 to about 30 mg/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. In an exemplary embodiment, additional active ingredients are those that are known or discovered to be effective in the treatment of conditions, disorders, or diseases mediated by histamine $H_3$ receptor and/or the serotonin transporter activity or that are active against another target associated with the particular condition, disorder, or disease, such as $H_1$ receptor antagonists, $H_2$ receptor antagonists, $H_3$ receptor antagonists, topiramate, and neurotransmitter modulators such as serotonin-norepinephrine reuptake inhibitors, selective serotonin reuptake inhibitors (SSRIs), noradrenergic reuptake inhibitors, non-selective serotonin re-uptake inhibitors (NSSRIs), acetylcholinesterase inhibitors (such as tetrahydroaminoacridine, Donepezil, Rivastigmine, or Galantamine), or modafinil. The combination may serve to increase efficacy (e.g., by including in the combination a compound potentiating the potency or effectiveness of a compound according to the invention), decrease one or more side effects, or decrease the required dose of the compound according to the invention.

More particularly, compounds of the invention in combination with modafinil are useful for the treatment of narcolepsy, excessive daytime sleepiness (EDS), Alzheimer's disease, depression, attention-deficit disorders, MS-related fatigue, post-anesthesia grogginess, cognitive impairment, schizophrenia, spasticity associated with cerebral palsy, age-related memory decline, idiopathic somnolence, or jet-lag. Preferably, the combination method employs doses of modafinil in the range of about 20 to 300 mg per dose.

The compounds of the invention are used, alone or in combination with one or more other active ingredients, to formulate pharmaceutical compositions of the invention. A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a compound of the invention and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the compounds of the invention may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.001 to about 100 mg/kg daily, or from about 0.001 to about 35 mg/kg daily, or from about 0.01 to about 10 mg/kg daily.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil, sesame oil, or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent.

Reductive amination with cyclic amines A2 on aryl aldehydes A1 gives amino bromides A3 that can then be converted to biaryl ethers A4 via $S_NAr$ reaction with 3-hydroxylbenzyl alcohol (A4). An $S_NAr$ reaction was not possible with some of our examples due to electronically unfavorable substitution of the aromatic ring. In those instances an Ullman coupling was used with CuI as the coupling agent. Swern oxidation of the alcohol followed by reductive amination with methylamine gives benzylic amines A5 in good yield. Alkylation of A5 with 4-thiomethyl-2'-bromoacetophenone followed by reduction of the ketone with $NaBH_4$ affords secondary alcohols A6. It is important to carry out the reduction immediately due to rapid oxidation of the amino ketone. Ring closure is affected by heating alcohols A6 in neat methanesulfonic acid to give compounds of Formula (I) in good yield. Where reactions give a mixture of regioisomers, the isomers are separated by chromatography.

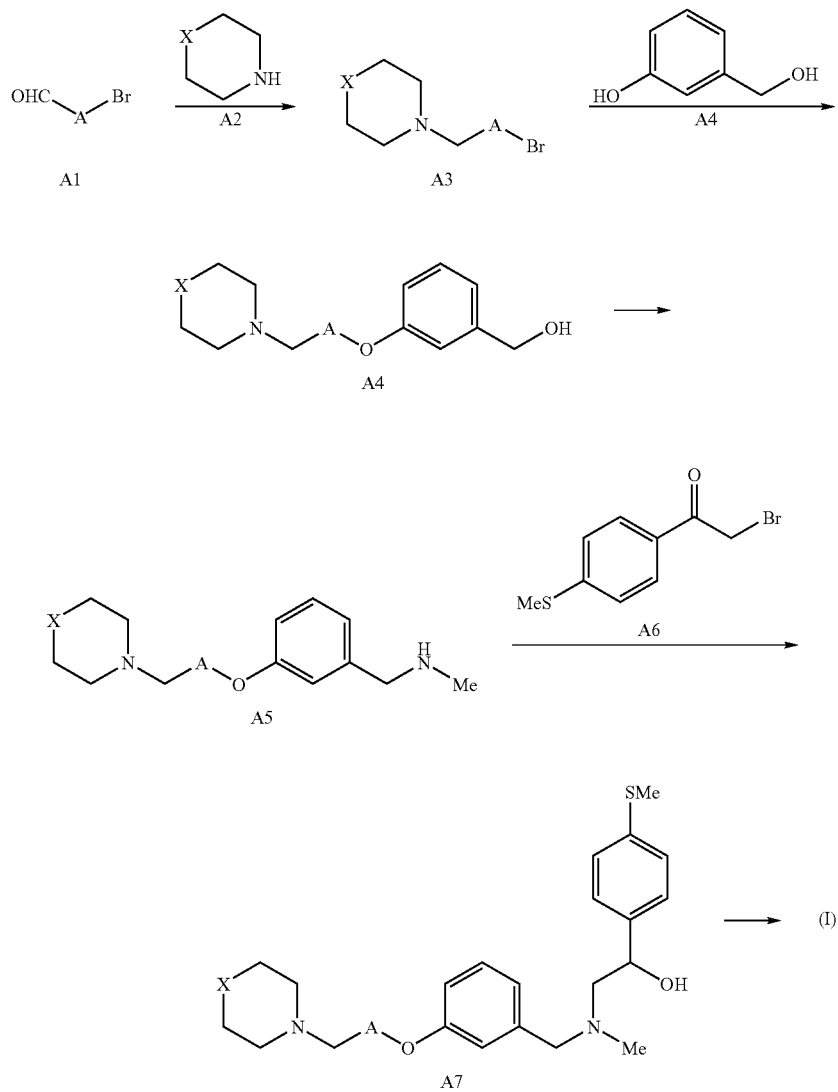

SCHEME A

SCHEME B

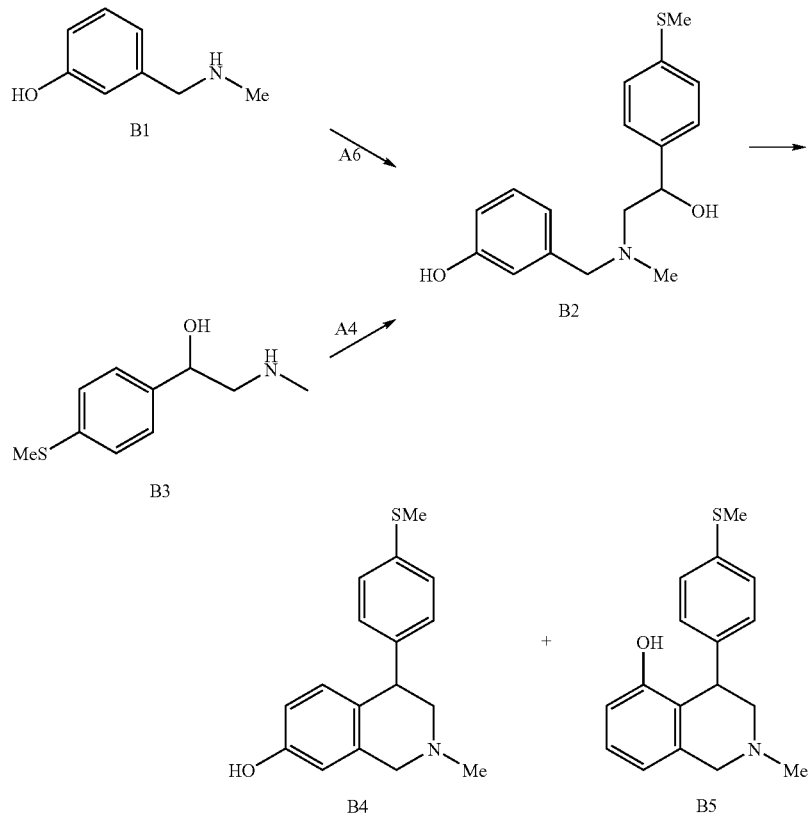

While the route shown in Scheme A is useful if variation of the pendant aryl ring at position four is desired, it is somewhat cumbersome if variation of the $H_3$ side chain is the objective. As we wished to avoid the use of protecting groups in the synthesis of the tetrahydroisoquinoline core, we envisioned amine B1 to be a useful intermediate. Amine B1 is readily prepared via reductive amination, but is troublesome to work with due to high water solubility and modest solubility in organic solvents. Amine B1 is not extracted efficiently from water with methylene chloride or ethyl acetate, but is readily extracted with n-butanol. Nevertheless, it is converted to phenol B2 via alkylation with ketone A6 and reduction of the corresponding ketone as described in Scheme A.

Recognizing that the high polarity of amine B1 was the source of difficulty with its manipulation, we desired an alternate route to B2 with more lipophillic intermediates. Alkylation of methylamine with 4-thiomethyl-2'-bromoacetophenone followed by immediate reduction of the ketone (one pot) gives B3 in reasonable yield, but also affords significant amounts of the dialkylated product (not shown). Increasing the equivalents of methylamine from five to twenty improves the yield of B3. Reductive amination of B3 with 3-hydroxybenzaldehyde gives B2. MSA mediated ring closure of B2 gives a 2:1 mixture of regioisomers B4 and B5, which were separated chromatographically. Attachment of the side chains onto B4 and B5 is accomplished by reaction with bromides A3 via $S_NAr$ or by Ullman coupling in the presence of CuI as described in Scheme A.

Compounds of Formula (I) may be converted to their corresponding salts using methods known to those skilled in the art. For example, amines of Formula (I) may be treated with trifluoroacetic acid, HCl, or citric acid in a solvent such as $Et_2O$, DCM, THF, or MeOH to provide the corresponding salt forms.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

Unless otherwise specified, normal phase flash column chromatography (FCC) was typically performed on silica gel ($SiO_2$) using 2 M $NH_3$ in $MeOH/CH_2Cl_2$ as the eluent.

Preparative Reverse Phase HPLC was performed under the following conditions: Instrument: Gilson®; Column: YMC-Pack ODS-A, 5 μm, 75×30 mm; flow rate: 25 mL/min; detection: λ=220 & 254 nm; gradient: 15% to 99% $CH_3CN/H_2O$ (0.05% TFA) over 20 min.

Mass spectra were obtained on an Agilent series 1100 MSD using electrospray ionization (ESI) in positive mode unless otherwise indicated. Calculated (calcd.) mass corresponds to the exact mass.

NMR spectra were obtained on either a Bruker model DPX400 (400 MHz), DPX500 (500 MHz), or DPX600 (600 MHz) spectrometer. The format of the $^1$H NMR data below is: chemical shift in ppm down field of the tetramethylsilane reference (multiplicity, coupling constant J in Hz, integration).

Chemical names were generated using ChemDraw Version 6.0.2 (CambridgeSoft, Cambridge, Mass.) or ACD/Name Version 9 (Advanced Chemistry Development, Toronto, Ontario, Canada).

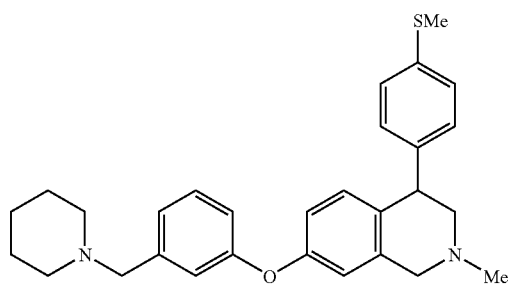

1A

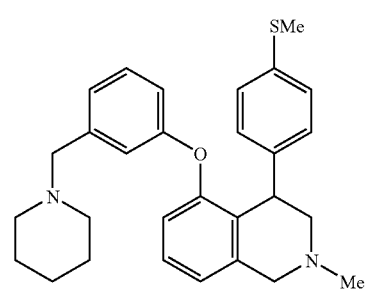

1B

Example 1

2-Methyl-4-(4-methylsulfanyl-phenyl)-7-(3-piperidin-1-ylmethyl-phenoxy)-1,2,3,4-tetrahydro-isoquinoline trifluoroacetic acid salt (1A) and 2-Methyl-4-(4-methylsulfanyl-phenyl)-5-(3-piperidin-1-ylmethyl-phenoxy)-1,2,3,4-tetrahydro-isoquinoline Trifluoroacetic Acid Salt (1 B).

Step A. 1-(3-Bromo-benzyl)-piperidine. To a mixture of 3-bromo-benzaldehyde (13.62 g, 73.61 mmol) and piperidine (8.75 mL, 88.3 mmol) in THF (375 mL) at 0° C. was added $Na(OAc)_3BH$ (24.28 g, 110.4 mmol) and the mixture was stirred at rt for 3 days. The solvent was evaporated and the residue taken up in 1 N NaOH and extracted with $CH_2Cl_2$. The combined organic layers were dried and concentrated. The crude product was purified by Kugelrohr distillation (b.p. 140° C. at 0.5 torr) to provide the desired product (16.73 g, 80%) as a colorless oil. MS (ESI): mass calcd. for $C_{12}H_{16}BrN$, 253.05; m/z found, 254.3, 256.3 $[M+H]^+$. $^1$H NMR (MeOD): 7.49-7.47 (m, 1H), 7.39-7.37 (m, 1H), 7.26-7.23 (m, 1H), 7.19 (t, J=7.7, 1H), 3.40 (s, 2H), 2.35 (br s, 4H), 1.58-1.51 (m, 4H), 1.44-1.37 (m, 2H).

Step B. [3-(3-Piperidin-1-ylmethyl-phenoxy)-phenyl]-methanol. To a 25 mL Smith-process vial were added 1-(3-bromo-benzyl)-piperidine (1.005 g, 3.969 mmol), 3-hydroxymethyl-phenol (1.034 g, 8.329 mmol), CuI (483.5 mg, 2.539 mmol), $Cs_2CO_3$ (2.599 g, 7.976 mmol) and N-methylpyrrolidine (5.5 mL). The vial was purged with $N_2$, the cap sealed, and the reaction mixture heated at 195° C. in a microwave reactor for 4 h. The mixture was diluted with $Et_2O$, washed with 1 N NaOH, water and brine, dried, and concentrated. Purification by FCC gave a yellow oil (908.7 mg, 77%). MS (ESI): mass calcd. for $C_{19}H_{23}NO_2$, 297.17; m/z found, 298.4 $[M+H]^+$. $^1$H NMR (MeOD): 7.44 (t, J=7.9, 1H), 7.34 (t, J=7.8, 1H), 7.22 (d, J=7.5, 1H), 7.16-7.10 (m, 2H), 7.09-7.00 (m, 2H), 6.94-6.89 (m, 1H), 4.58 (s, 2H), 4.24 (s, 2H), 3.44-3.37 (m, 2H), 2.95-2.86 (m, 2H), 1.92-1.84 (m, 2H), 1.81-1.67 (m, 3H), 1.52-1.41 (m, 1H).

Step C. 3-(3-Piperidin-1-ylmethyl-phenoxy)-benzaldehyde. To a solution of DMSO (0.52 mL) and $CH_2Cl_2$ (20 mL) at −78° C. was added oxalyl chloride (2 M in $CH_2Cl_2$; 2.0 mL, 40 mmol) and the mixture was stirred for 30 min. A solution of [3-(3-piperidin-1-ylmethyl-phenoxy)-phenyl]-methanol (908 mg, 30.5 mmol) in $CH_2Cl_2$ (10 mL) was then added. The mixture was stirred for 30 min and then $Et_3N$ (2.2 mL, 16 mmol) was added. After an additional 1 h at −78° C., the mixture was diluted with EtOAc, washed with 1 N NaOH and brine, dried, and concentrated. Purification by FCC gave a yellow oil (416.0 mg, 86%). MS (ESI): mass calcd. for $C_{19}H_{21}NO_2$, 295.16; m/z found, 296.4 $[M+H]^+$. $^1$H NMR (acetone-$d_6$): 10.00 (s, 1H), 7.67 (d, J=8.3, 1H), 7.61 (t, J=7.9, 1H), 7.45 (s, 1H), 7.37-7.30 (m, 2H), 7.14 (d, J=7.2, 1H), 7.07 (s, 1H), 6.93 (d, J=7.7, 1H), 3.44 (s, 2H), 2.34 (br s, 4H), 1.53-1.46 (m, 4H), 1.42-1.35 (m, 2H).

Step D. Methyl-[3-(3-piperidin-1-ylmethyl-phenoxy)-benzyl]-amine. To a solution of 3-(3-piperidin-1-ylmethyl-phenoxy)-benzaldehyde (0.56 g, 1.9 mmol) in MeOH (4.0 mL) at 0° C. were added $MeNH_2$ (40% in $H_2O$; 0.35 mL, 4.0 mmol) followed by $NaBH_4$ (170.6 mg, 4.510 mmol). The mixture was stirred at 0° C. for 3.5 h, then diluted with 1 N NaOH, stirred for 1 h, and extracted with CH₂Cl₂. The combined organic layers were dried and concentrated to give a pale yellow oil (410.0 mg, 98%). MS (ESI): mass calcd. for $C_{20}H_{26}N_2O$, 310.20; m/z found, 311.4 [M+H]⁺. ¹H NMR (MeOD): 7.29-7.22 (m, 2H), 7.06-7.01 (m, 2H), 6.98-6.94 (m, 2H), 6.87-6.83 (m, 2H), 3.63 (s, 2H), 3.41 (s, 2H), 2.42-2.34 (m, 3H), 2.31 (s, 3H), 1.59-1.53 (m, 4H), 1.46-1.40 (m, 2H).

Step E. 2-{Methyl-[3-(3-piperidin-1-ylmethyl-phenoxy)-benzyl]-amino}-1-(4-methylsulfanyl-phenyl)-ethanone. To a solution of methyl-[3-(3-piperidin-1-ylmethyl-phenoxy)-benzyl]-amine (530 mg, 1.71 mmol) and diisopropyl-ethylamine (0.89 mL, 5.1 mmol) in THF (17.0 mL) was added 2-bromo-1-(4-methylsulfanyl-phenyl)-ethanone (508.6 mg, 2.075 mmol). After 18 h, the mixture was concentrated and carried forward without purification. MS (ESI): mass calcd. for $C_{29}H_{34}N_2O_2S$, 474.23; m/z found, 475.5 [M+H]⁺.

Step F. 2-{Methyl-[3-(3-piperidin-1-ylmethyl-phenoxy)-benzyl]-amino}-1-(4-methylsulfanyl-phenyl)-ethanol. To a solution of 2-{methyl-[3-(3-piperidin-1-ylmethyl-phenoxy)-benzyl]-amino}-1-(4-methylsulfanyl-phenyl)-ethanone and EtOH (17.0 mL) was added NaBH₄ (242.6 mg, 6.413 mmol). After 1 h, the mixture was diluted with 1 N NaOH, extracted with CH₂Cl₂, dried, and concentrated. Purification by FCC gave a colorless oil (656.4 mg, 81% over 2 steps). MS (ESI): mass calcd. for $C_{29}H_{36}N_2O_2S$, 476.25; m/z found, 477.5 [M+H]⁺. ¹H NMR (MeOD): 7.30-7.22 (m, 2H), 7.20 (d, J=8.3, 2H), 7.16 (d, J=8.4, 2H), 7.05-7.00 (m, 2H), 6.96-6.92 (m, 2H), 6.88-6.83 (m, 2H), 4.72-4.68 (m, 1H), 3.59-3.49 (m, 2H), 3.39 (s, 2H), 2.62-2.56 (m, 1H), 2.49-2.41 (m, 1H), 2.40 (s, 3H), 2.39-2.30 (m, 4H), 2.25 (s, 3H), 1.57-1.50 (m, 4H), 1.44-1.36 (m, 2H).

Step G. A mixture of 2-{methyl-[3-(3-piperidin-1-ylmethyl-phenoxy)-benzyl]-amino}-1-(4-methylsulfanyl-phenyl)-ethanol (561.9 mg, 1.179 mmol), and MSA (0.46 mL, 7.1 mmol) in CH₂Cl₂ (2.40 mL) was stirred for 18 h. The mixture was diluted with CH₂Cl₂, washed with 1 N NaOH and brine, dried, and concentrated. Purification by FCC gave a colorless oil (183.4 mg, 33%). The oil was purified by preparative HPLC to give the title compounds.

Example 1A

Yield: 185.3 mg. MS (ESI): mass calcd. for $C_{29}H_{34}N_2OS$, 458.24; m/z found, 459.5 [M+H]⁺. ¹H NMR (MeOD): 7.46 (t, J=7.9, 1H), 7.29-7.24 (m, 3H), 7.23-7.17 (m, 3H), 7.11-7.07 (m, 1H), 6.79 (br s, 1H), 6.91-6.86 (m, 2H), 4.59-4.53 (m, 3H), 4.12 (s, 2H), 3.84-3.78 (m, 1H), 3.55-3.40 (m, 3H), 2.92 (s, 3H), 2.97-2.89 (m, 2H), 2.31 (s, 3H), 1.93-1.86 (m, 2H), 1.84-1.70 (m, 3H), 1.53-1.45 (m, 1H), 1.38-1.26 (m, 1H).

Example 1B

Yield: 49.6 mg. MS (ESI): mass calcd. for $C_{29}H_{34}N_2OS$, 458.24; m/z found, 459.5 [M+H]⁺. ¹H NMR (MeOD): 7.38 (t, J=7.9, 1H), 7.30-7.22 (m, 1H), 7.16-7.02 (m, 6H), 6.86 (d, J=8.1, 1H), 6.78-6.60 (m, 2H), 4.71-4.44 (m, 3H), 4.18-4.10 (m, 2H), 3.94-3.82 (m, 2H), 2.30 (s, 3H), 1.96-1.88 (m, 2H), 1.85-1.64 (m, 3H), 1.54-1.43 (m, 1H), 1.41-1.25 (m, 1H).

The compounds in Examples 2-4 were prepared using methods analogous to those described in Example 1.

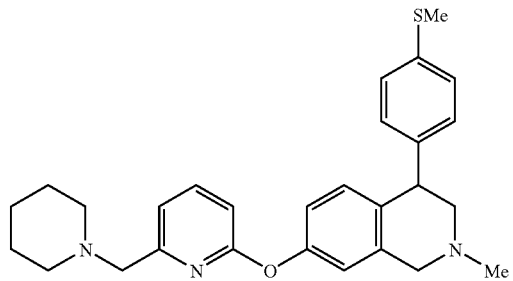

Example 2

2-Methyl-4-(4-methylsulfanyl-phenyl)-7-(6-piperidin-1-ylmethyl-pyridin-2-yloxy)-1,2,3,4-tetrahydro-isoquinoline Trifluoroacetic Acid Salt MS (ESI): mass calcd. for $C_{28}H_{33}N_3OS$, 459.23; m/z found, 460.5 [M+H]⁺. ¹H NMR (MeOD): 7.71 (t, J=8.0, 1H), 7.17 (d, J=8.3, 2H), 7.17 (d, J=7.4, 1H), 6.87-6.85 (m, 1H), 6.81-6.75 (m, 2H), 6.71 (d, J=8.2, 1H), 5.44 (s, 1H), 4.26-4.20 (m, 1H), 3.76 (d, J=15.1, 1H), 3.55 (d, J=15.0, 1H), 3.46 (s, 2H), 3.04-2.99 (m, 1H), 2.51-2.34 (m, 1H), 1.55-1.50 (m, 5H), 1.44-1.37 (m, 2H).

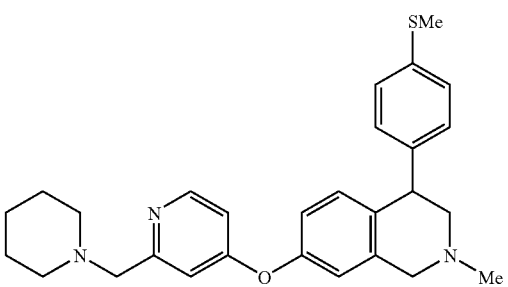

A

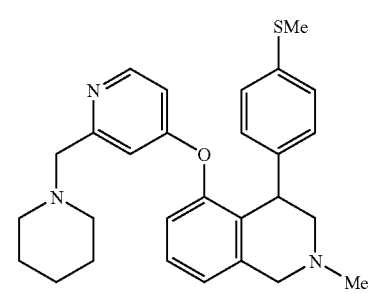

B

Example 3

2-2-Methyl-4-(4-methylsulfanyl-phenyl)-7-(2-piperidin-1-ylmethyl-pyridin-4-yloxy)-1,2,3,4-tetrahydro-isoquinoline Trifluoroacetic Acid Salt (3A) and 2-Methyl-4-(4-methylsulfanyl-phenyl)-5-(2-piperidin-1-ylmethyl-pyridin-4-yloxy)-1,2,3,4-tetrahydro-isoquinoline Trifluoroacetic Acid Salt (3B).

Example 3A

MS (ESI): mass calcd. for $C_{28}H_{33}N_3OS$, 459.23; m/z found, 460.4 $[M+H]^+$. $^1H$ NMR (MeOD): 8.30 (d, J=5.8, 1H), 7.19 (d, J=8.3, 2H), 7.13 (d, J=8.3, 2H), 7.07 (d, J=2.4, 1H), 6.93-6.91 (m, 1H), 6.90 (d, J=2.4, 1H), 6.83-6.79 (m, 2H), 4.30-4.25 (m, 1H), 3.80 (d, J=15.2, 1H), 3.59 (d, J=15.2, 1H), 3.45 (s, 2H), 3.10-3.04 (m, 1H), 2.57-2.52 (m, 1H), 2.43-2.36 (m, 10H), 1.57-1.51 (m, 4H), 1.47-1.40 (m, 2H).

Example 3B

MS (ESI): mass calcd. for $C_{28}H_{33}N_3OS$, 459.23; m/z found, 460.4 $[M+H]^+$. $^1H$ NMR (MeOD): 7.96 (d, J=5.8, 1H), 7.21 (t, J=7.8, 1H), 7.05 (d, J=7.6, 1H), 6.83-6.80 (m, 4H), 6.77 (d, J=7.9, 1H), 6.52-6.50 (m, 1H), 6.32 (dd, J=5.8, 2.5, 1H), 4.09 (t, J=6.1, 1H), 3.71 (d, J=15.1, 1H), 3.55 (d, J=15.1, 1H), 3.38 (s, 2H), 2.86-2.81 (m, 1H), 2.52-2.47 (m, 1H), 2.29-2.24 (m, 7H), 2.26 (s, 3H), 1.50-1.45 (m, 4H), 1.40-1.32 (m, 2H).

Example 4

2-Methyl-4-(4-methylsulfanyl-phenyl)-7-(5-piperidin-1-ylmethyl-pyridin-3-yloxy)-1,2,3,4-tetrahydro-isoquinoline Trifluoroacetic Acid Salt (4A) and 2-Methyl-4-(4-methylsulfanyl-phenyl)-5-(5-piperidin-1-ylmethyl-pyridin-3-yloxy)-1,2,3,4-tetrahydro-isoquinoline Trifluoroacetic Acid Salt (4B)

Example 4A

MS (ESI): mass calcd. for $C_{28}H_{33}N_3OS$, 459.23; m/z found, 460.4 $[M+H]^+$. $^1H$ NMR (MeOD): 8.20 (dd, J=23.1, 1.4, 2H), 7.44-7.41 (m, 1H), 7.21 (d, J=8.3, 2H), 6.78 (dd, J=8.5, 2.4, 1H), 4.29-4.24 (m, 1H), 3.80 (d, J=15.2, 1H), 3.59 (d, J=15.2, 1H), 3.44 (s, 2H), 3.11-3.06 (m, 1H), 2.57-2.52 (m, 1H), 2.46-2.34 (m, 10H), 1.60-1.55 (m, 4H), 1.49-1.42 (m, 2H).

Example 4B

MS (ESI): mass calcd. for $C_{28}H_{33}N_3OS$, 459.23; m/z found, 460.4 $[M+H]^+$. $^1H$ NMR (MeOD): 8.00 (s, 1H), 7.73-7.71 (m, 1H), 7.21 (t, J=7.8, 1H), 7.03 (d, J=7.7, 1H), 6.94 (d, J=8.2, 2H), 6.89 (d, J=8.3, 2H), 6.80-6.77 (m, 1H), 6.71 (d, J=8.0, 1H), 4.23 (t, J=6.2, 1H), 3.73 (d, J=15.1, 1H), 3.61-3.56 (m, 1H), 3.36 (s, 2H), 3.01-2.97 (m, 1H), 2.64-2.60 (m, 1H), 2.46-2.41 (m, 1H), 2.40 (s, 3H), 2.36-2.28 (m, 6H), 1.60-1.52 (m, 4H), 1.49-1.43 (m, 2H).

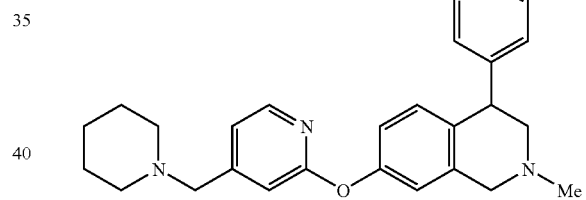

A

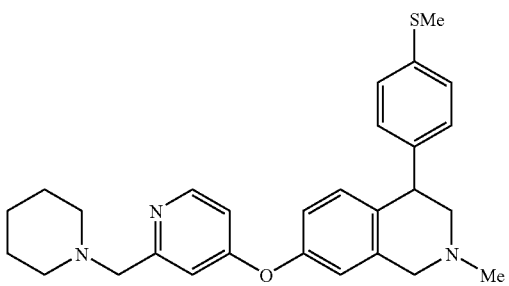

B

Example 5

2-Methyl-4-(4-methylsulfanyl-phenyl)-7-(4-piperidin-1-ylmethyl-pyridin-2-yloxy)-1,2,3,4-tetrahydro-isoquinoline Step A. 2-Bromo-1-(4-methylsulfanyl-phenyl)-ethanone. To a solution of 1-(4-methylsulfanyl-phenyl)-ethanone (200.29 g, 1.2051 mmol) in MeOH (720 mL) was added bromine (61.5 mL, 1.20 mmol) dropwise over 1 h via an additional funnel. After addition was complete, water was added and the mixture was stirred vigorously. Vacuum filtration gave the desired product (285.53 g, 97%) as a solid. MS (ESI): mass calcd. for $C_9H_9BrOS$, 243.96; m/z found, 245.2, 247.2 $[M+H]^+$. $^1H$ NMR (acetone-$d_6$): 7.98 (d, J=8.7, 2H), 7.40 (d, J=8.7, 2H), 4.72 (s, 2H), 2.59 (s, 3H).

Step B. 2-Methylamino-1-(4-methylsulfanyl-phenyl)-ethanol. To a solution of EtOH (400 mL) and $MeNH_2$ (40% in $H_2O$; 63.5 mL, 815.9 mmol), 2-bromo-1-(4-methylsulfanyl-phenyl)-ethanone (10.08 g, 40.79 mmol) was added slowly with vigorous stirring over 20 min. $NaBH_4$ (4.764 g, 122.4 mmol) was then added portionwise and the reaction was stirred at rt for 18 h. The reaction mixture was concentrated and purified by FCC to give the desired product (6.339 g, 78%). MS (ESI): mass calcd. for $C_{10}H_{15}NOS$, 197.09; m/z found, 198.1 [M+H]$^+$. $^1$H NMR (MeOD): 7.31 (d, J=8.2, 2H), 7.26 (d, J=8.4, 2H), 4.76-4.72 (m, 1H), 2.76-2.72 (m, 1H), 2.70-2.65 (m, 1H), 2.47 (s, 3H), 2.41 (s, 3H).

Step C. 3-({[2-Hydroxy-2-(4-methylsulfanyl-phenyl)-ethyl]-methyl-amino}-methyl)-phenol. To a mixture of 2-methylamino-1-(4-methylsulfanyl-phenyl)-ethanol (3.40 g, 17.2 mmol), 3-hydroxy-benzaldehyde (2.810 g, 22.40 mmol), and acetic acid (0.99 mL, 17 mmol) in THF (50 mL) at 0° C. was added Na(OAc)$_3$BH (8.568 g, 43.08 mmol) and the mixture was stirred at rt for 3 days. The solvent was evaporated and the residue taken up in 1 N NaOH and extracted with CH$_2$Cl$_2$. The combined organic layers were dried and concentrated. Purification by FCC gave the desired product (3.51 g, 78%) as a solid. MS (ESI): mass calcd. for $C_{17}H_{21}NO_2S$, 303.13; m/z found, 304.3 [M+H]$^+$. $^1$H NMR (MeOD): 7.24 (d, J=8.2, 2H), 7.20 (d, J=8.3, 2H), 7.13 (t, J=7.8, 1H), 6.80 (s, 1H), 6.77 (d, J=7.4, 1H), 6.72-6.71 (m, 1H), 4.78-4.74 (m, 1H), 3.56 (d, J=13.0, 1H), 3.48 (d, J=13.0, 1H), 2.66-2.61 (m, 1H), 2.51-2.47 (m, 1H), 2.41 (s, 3H), 2.28 (s, 3H).

Step D. 2-Methyl-4-(4-methylsulfanyl-phenyl)-1,2,3,4-tetrahydro-isoquinolin-7-ol. The title compound was prepared in an analogous fashion to Example 1, Step G, with heating at 50° C. to give the desired product (3.08 g, 67%). MS (ESI): mass calcd. for $C_{17}H_{19}NOS$, 285.12; m/z found, 286.3 [M+H]$^+$. $^1$H NMR (MeOD): 7.21 (d, J=6.9, 2H), 7.10 (d, J=7.1, 2H), 6.63 (d, J=9.1, 1H), 6.58-6.54 (m, 2H), 4.24-4.18 (m, 1H), 3.82 (d, J=14.9, 1H), 3.61 (d, J=14.9, 1H), 3.15-3.10 (m, 1H), 2.57 (t, J=11.1, 1H), 2.48 (s, 3H), 2.46 (s, 3H).

Step E. To a Smith-process vial were added 2-methyl-4-(4-methylsulfanyl-phenyl)-1,2,3,4-tetrahydro-isoquinolin-7-ol (305.8 mg, 1.051 mmol), 2-bromo-4-piperidin-1-ylmethyl-pyridine (338.7 mg, 1.314 mmol), Cs$_2$CO$_3$ (684.9 mg, 2.102 mmol) and N-methylpyrrolidine (2.10 mL). The vial was purged with N$_2$, the cap sealed, and the reaction mixture heated at 150° C. in a microwave reactor for 2 h. The mixture was diluted with Et$_2$O, washed with 1 N NaOH, water and brine, dried, and concentrated. Purification by FCC gave the desired product (237.5 mg, 48%). MS (ESI): mass calcd. for $C_{28}H_{33}N_3OS$, 459.23; m/z found, 460.3 [M+H]$^+$. $^1$H NMR (acetone-d$_6$): 8.03 (d, J=5.1, 1H), 7.23-7.19 (m, 4H), 7.04 (d, J=5.1, 1H), 6.94 (s, 1H), 6.90-6.89 (m, 1H), 6.88-6.83 (m, 2H), 4.19 (t, J=6.2, 1H), 3.63 (q, J=15.1, 2H), 3.46 (s, 2H), 2.92-2.88 (m, 1H), 2.62-2.58 (m, 1H), 2.47 (s, 3H), 2.41-2.35 (m, 4H), 2.35 (s, 3H), 1.56 (quintet, J=5.5, 4H), 1.46-1.40 (m, 2H).

The compounds in Examples 6-13 were prepared using methods analogous to those described in Example 5, with exceptions as noted.

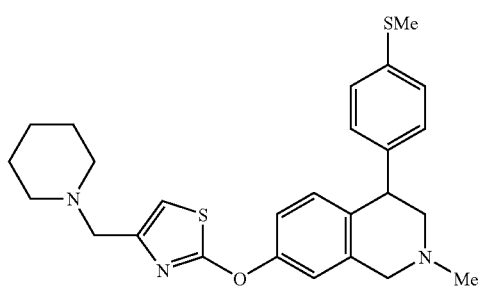

Example 6

2-Methyl-4-(4-methylsulfanyl-phenyl)-7-(4-piperidin-1-ylmethyl-thiazol-2-yloxy)-1,2,3,4-tetrahydro-isoquinoline MS (ESI): mass calcd. for $C_{26}H_{31}N_3OS_2$, 465.19; m/z found, 466.4 [M+H]$^+$. $^1$H NMR (MeOD): 7.24-7.21 (m, 2H), 7.15-7.10 (m, 3H), 7.03-7.00 (m, 1H), 6.91-6.88 (m, 1H), 6.88-6.86 (m, 1H), 4.30-4.26 (m, 1H), 3.84 (d, J=15.3, 1H), 3.62 (d, J=15.3, 1H), 3.48-3.45 (m, 2H), 3.12-3.07 (m, 1H), 2.59-2.54 (m, 1H), 2.51-2.44 (m, 10H), 1.63-1.53 (m, 4H), 1.49-1.41 (m, 2H).

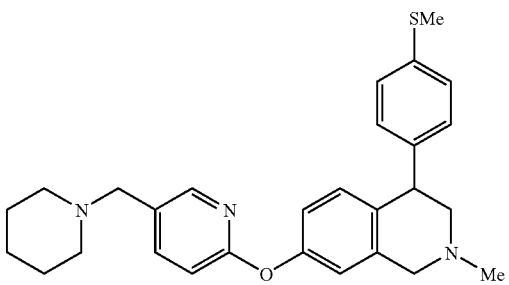

Example 7

2-Methyl-4-(4-methylsulfanyl-phenyl)-7-(5-piperidin-1-ylmethyl-pyridin-2-yloxy)-1,2,3,4-tetrahydro-isoquinoline MS (ESI): mass calcd. for $C_{28}H_{33}N_3OS$, 459.23; m/z found, 460.4 [M+H]$^+$. $^1$H NMR (MeOD): 7.91 (s, 1H), 7.64 (dd, J=8.4, 2.1, 1H), 7.07 (d, J=8.2, 2H), 7.00 (d, J=8.2, 2H), 6.78-6.73 (m, 2H), 6.72-6.65 (m, 2H), 4.15-4.10 (m, 1H), 3.67 (d, J=15.1, 1H), 3.45 (d, J=15.1, 1H), 3.32 (s, 2H), 3.24 (s, 2H), 2.96-2.91 (m, 1H), 2.41 (t, J=11.4, 1H), 2.32-2.25 (m, 9H), 1.48-1.43 (m, 4H), 1.35-1.29 (m, 2H).

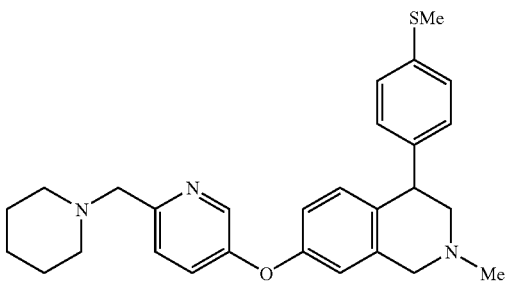

Example 8

2-Methyl-4-(4-methylsulfanyl-phenyl)-7-(6-piperidin-1-ylmethyl-pyridin-3-yloxy)-1,2,3,4-tetrahydro-isoquinoline The title compound was prepared according to Example 1, Step B. MS (ESI): mass calcd. for $C_{28}H_{33}N_3OS$, 459.23; m/z found, 460.4 [M+H]$^+$. $^1$H NMR (CDCl$_3$): 8.34 (d, J=2.8, 1H), 7.55 (d, J=8.5, 1H), 7.29-7.25 (m, 1H), 7.22 (d, J=8.3, 2H), 7.13 (d, J=8.2, 2H), 6.91 (d, J=8.3, 1H), 6.83-6.78 (m, 2H), 4.35-4.31 (m, 1H), 4.25-4.19 (m, 2H), 3.96-3.91 (m, 1H), 3.81-3.75 (m, 1H), 3.35-3.15 (m, 4H), 2.75-2.69 (m, 2H), 2.58 (s, 3H), 2.48 (s, 3H), 1.95-1.86 (m, 5H), 1.75-1.50 (m, 1H).

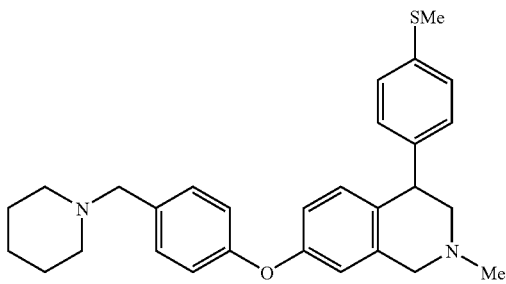

Example 9

2-Methyl-4-(4-methylsulfanyl-phenyl)-7-(4-piperidin-1-ylmethyl-phenoxy)-1,2,3,4-tetrahydro-isoquinoline The title compound was prepared according to Example 1, Step B. MS (ESI): mass calcd. for $C_{29}H_{34}N_2OS$, 458.24; m/z found, 459.4 [M+H]$^+$. $^1$H NMR (CDCl$_3$): 7.33 (d, J=8.6, 2H), 7.19 (d, J=8.3, 2H), 7.11 (d, J=8.3, 2H), 6.95 (d, J=8.6, 2H), 6.85 (d, J=8.2, 1H), 6.80-6.73 (m, 2H), 4.31-4.25 (m, 1H), 4.14-4.05 (m, 3H), 3.88-3.81 (m, 1H), 3.78-3.66 (m, 1H), 3.18-3.10 (m, 2H), 2.70-2.62 (m, 3H), 2.50 (s, 3H), 2.45 (s, 3H), 1.96-1.84 (m, 5H), 1.82-1.40 (m, 1H).

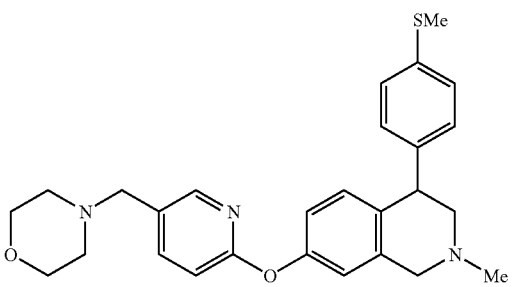

Example 10

2-Methyl-4-(4-methylsulfanyl-phenyl)-7-(5-morpholin-4-ylmethyl-pyridin-2-yloxy)-1,2,3,4-tetrahydro-isoquinoline MS (ESI): mass calcd. for $C_{27}H_{31}N_3O_2S$, 461.21; m/z found, 462.3 [M+H]$^+$. $^1$H NMR (MeOD): 8.06 (s, 1H), 7.81 (d, J=8.4, 2.1, 1H), 7.22 (d, J=8.2, 2H), 7.15 (d, J=8.2, 2H), 6.95-6.90 (m, 2H), 6.87-6.83 (m, 2H), 4.36-4.31 (m, 1H), 3.98 (d, J=15.2, 1H), 3.82 (d, J=15.2, 1H), 3.69-3.64 (m, 4H), 3.50 (s, 2H), 3.27-3.23 (m, 1H), 2.78 (t, J=11.5, 1H), 2.58 (s, 3H), 2.48-2.42 (m, 7H).

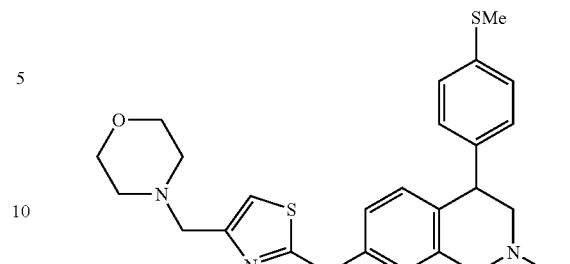

Example 11

2-Methyl-4-(4-methylsulfanyl-phenyl)-7-(4-morpholin-4-ylmethyl-thiazol-2-yloxy)-1,2,3,4-tetrahydro-isoquinoline MS (ESI): mass calcd. for $C_{25}H_{29}N_3O_2S_2$, 467.17; m/z found, 468.3 [M+H]$^+$. $^1$H NMR (MeOD): 7.21 (d, J=8.4, 2H), 7.14-7.08 (m, 3H), 7.00 (dd, J=8.5, 2.5, 1H), 6.90-6.86 (m, 2H), 4.29-4.25 (m, 1H), 3.83 (d, J=15.2, 1H), 3.69 (t, J=4.7, 4H), 3.61 (d, J=15.2, 1H), 3.47 (s, 2H), 3.10-3.06 (m, 1H), 2.58-2.53 (m, 1H), 2.52-2.48 (m, 4H), 2.45 (s, 3H), 2.44 (s, 3H).

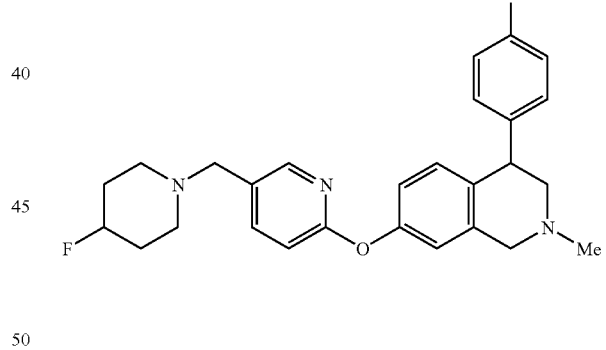

Example 12

7-[5-(4-Fluoro-piperidin-1-ylmethyl)-pyridin-2-yloxy]-2-methyl-4-(4-methylsulfanyl-phenyl)-1,2,3,4-tetrahydro-isoquinoline MS (ESI): mass calcd. for $C_{28}H_{32}FN_3OS$, 477.23; m/z found, 478.2 [M+H]$^+$. $^1$H NMR (MeOD): 8.02 (d, J=2.2, 1H), 7.72 (dd, J=8.5, 2.4, 1H), 7.15 (d, J=8.4, 2H), 7.09 (d, J=8.4, 2H), 6.88-6.84 (m, 2H), 6.81-6.75 (m, 2H), 4.66-4.54 (m, 1H), 4.24-4.20 (m, 1H), 3.74 (d, J=15.1, 1H), 3.54 (d, J=15.1, 1H), 3.43 (s, 2H), 3.03-2.98 (m, 1H), 2.56-2.46 (m, 3H), 2.39-2.30 (m, 8H), 1.88-1.72 (m, 4H).

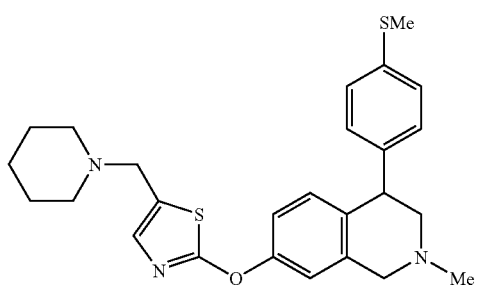

Example 13

2-Methyl-4-(4-methylsulfanyl-phenyl)-7-(5-piperidin-1-ylmethyl-thiazol-2-yloxy)-1,2,3,4-tetrahydroisoquinoline $^1$H NMR (CDCl$_3$): 7.20 (d, J=8.4, 2H), 7.12 (d, J=8.3, 2H), 7.00-6.96 (m, 3H), 6.90 (d, J=8.5, 1H), 4.22-4.18 (m, 1H), 3.73 (d, J=15.1, 1H), 3.62 (d, J=15.1, 1H), 3.53 (s, 2H), 3.02-2.97 (m, 1H), 2.57-2.52 (m, 1H), 2.47 (s, 3H), 2.42-2.37 (m, 7H), 1.57 (quintet, J=5.6, 4H), 1.45-1.40 (m, 2H).

Biological Methods:

A. H$_3$ Receptor Binding

Binding of compounds to the cloned human H$_3$ receptors, stably expressed in SK-N-MC cells, was performed as described by Barbier, A. J. et al. (Br. J. Pharmacol. 2004, 143(5), 649-661). Data for compounds tested in this assay are presented in Table 1.

TABLE 1

| Ex. | Human H$_3$ K$_i$ (nM) |
|---|---|
| 1A | 18.0 |
| 1B | 253 |
| 2 | 51 |
| 3A | 323 |
| 3B | 265 |
| 4A | 109 |
| 4B | 511 |
| 5 | 34.3 |
| 6 | 20.7 |
| 7 | 8.2 |
| 8 | 24.3 |
| 9 | 22.7 |
| 10 | 260 |
| 11 | 201 |
| 12 | 110 |
| 13 | 20.7 |

B. Rat Brain SERT

A rat brain without cerebellum (Zivic Laboratories, Inc.-Pittsburgh, Pa.) was homogenized in a 52.6 mM Tris pH 8/126.4 mM NaCl/5.26 mM KCl mixture and centrifuged at 1,000 rpm for 5 min. The supernatant was removed and re-centrifuged at 15,000 rpm for 30 min. Pellets were re-homogenized in a 52.6 mM Tris pH8/126.4 mM NaCl/5.26 mM KCl mixture. Membranes were incubated with 0.6 nM [$^3$H]-Citalopram plus/minus test compounds for 60 min at 25° C. and harvested by rapid filtration over GF/C glass fiber filters (pre-treated with 0.3% polyethylenimine) followed by four washes with ice-cold buffer. Nonspecific binding was defined in the presence of 100 μM fluoxetine. IC$_{50}$ values were determined by a single site curve-fitting program (GraphPad, San Diego, Calif.) and converted to K$_i$ values based on a [$^3$H]-Citalopram K$_d$ of 0.6 nM and a ligand concentration of 0.6 nM. Data for compounds tested are presented in Table 2.

C. Human SERT

Homogenized HEK293 (Human Embryonic Kidney) membranes expressing the human SERT were incubated with $^3$H-citalopram (SERT) at rt for 1 h in 50 mM Tris, 120 mM NaCl, 5 mM KCl (pH 7.4). Nonspecific binding was determined in the presence of 10 μM fluoxetine for the SERT. The membranes were washed and the radioactivity was counted as above. Calculations for K$_i$ at the SERT were based on a K$_d$ value for $^3$H-citalopram and a ligand concentration of 3.1 nM. Data for compounds tested are presented in Table 2.

TABLE 2

| Ex. | Rat SERT K$_i$ (nM) | Human SERT K$_i$ (nM) |
|---|---|---|
| 1A | 11.7 | 17.7 |
| 1B | 403 | 616 |
| 2 | 11.7 | 22.0 |
| 3A | 25.7 | 10.4 |
| 3B | 182 | 157 |
| 4A | 9.7 | 8.3 |
| 4B | 174 | 262 |
| 5 | 8.7 | 2.4 |
| 6 | 5.2 | 4.3 |
| 7 | 4.5 | 2.3 |
| 8 | 7.5 | 8.0 |
| 9 | 4.3 | 3.8 |
| 10 | 11 | 7.9 |
| 14 | 14 | 15.5 |
| 12 | 14.3 | 6.5 |
| 13 | 4.0 | 3.2 |

What is claimed is:

1. A compound of Formula (I):

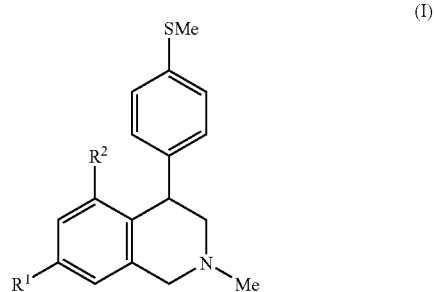

wherein
one of R$^1$ and R$^2$ is H and the other is

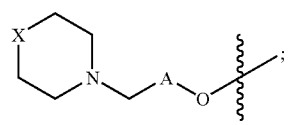

where A is phenyl, pyridyl, or thiazolyl; and
X is CH$_2$, O, or CHF;
or a pharmaceutically acceptable salt, or a pharmaceutically acceptable prodrug of such compound.

2. A compound as defined in claim 1, wherein R¹ is

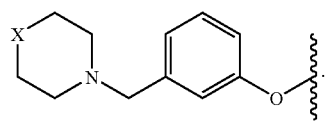

3. A compound as defined in claim 1, wherein R¹ is

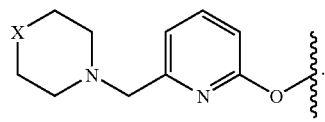

4. A compound as defined in claim 1, wherein R¹ is

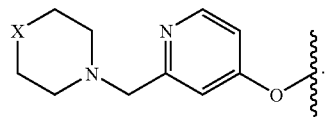

5. A compound as defined in claim 1, wherein R¹ is

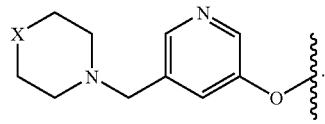

6. A compound as defined in claim 1, wherein R¹ is

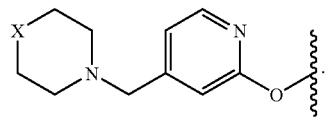

7. A compound as defined in claim 1, wherein R¹ is

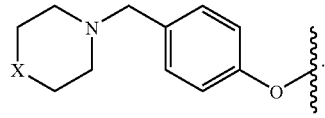

8. A compound as defined in claim 1, wherein R¹ is

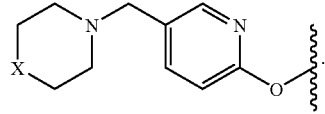

9. A compound as defined in claim 1, wherein R¹ is

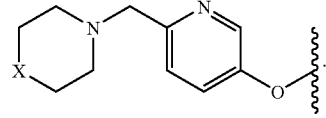

10. A compound as defined in claim 1, wherein R¹ is

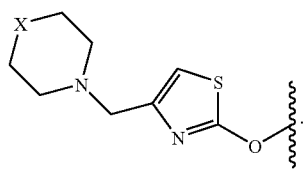

11. A compound as defined in claim 1, wherein R¹ is

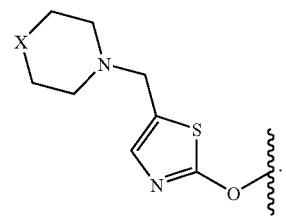

12. A compound selected from the group consisting of:
2-Methyl-4-(4-methylsulfanyl-phenyl)-7-(3-piperidin-1-ylmethyl-phenoxy)-1,2,3,4-tetrahydro-isoquinoline; 2-Methyl-4-(4-methylsulfanyl-phenyl)-5-(3-piperidin-1-ylmethyl-phenoxy)-1,2,3,4-tetrahydro-isoquinoline; 2-Methyl-4-(4-methylsulfanyl-phenyl)-7-(6-piperidin-1-ylmethyl-pyridin-2-yloxy)-1,2,3,4-tetrahydro-isoquinoline; 2-2-Methyl-4-(4-methylsulfanyl-phenyl)-7-(2-piperidin-1-ylmethyl-pyridin-4-yloxy)-1,2,3,4-tetrahydro-isoquinoline; 2-Methyl-4-(4-methylsulfanyl-phenyl)-5-(2-piperidin-1-ylmethyl-pyridin-4-yloxy)-1,2,3,4-tetrahydro-isoquinoline; 2-Methyl-4-(4-methylsulfanyl-phenyl)-7-(5-piperidin-1-ylmethyl-pyridin-3-yloxy)-1,2,3,4-tetrahydro-isoquinoline; 2-Methyl-4-(4-methylsulfanyl-phenyl)-5-(5-piperidin-1-ylmethyl-pyridin-3-yloxy)-1,2,3,4-tetrahydro-isoquinoline; 2-Methyl-4-(4-methylsulfanyl-phenyl)-7-(4-piperidin-1-ylmethyl-pyridin-2-yloxy)-1,2,3,4-tetrahydro-isoquinoline; 2-Methyl-4-(4-methylsulfanyl-phenyl)-7-(4-piperidin-1-ylmethyl-thiazol-2-yloxy)-1,2,3,4-tetrahydro-isoquinoline; 2-Methyl-4-(4-methylsulfanyl-phenyl)-7-(5-piperidin-1-ylmethyl-pyridin-2-yloxy)-1,2,3,4-tetrahydro-isoquinoline; 2-Methyl-4-(4-methylsulfanyl-phenyl)-7-(6-piperidin-1-ylmethyl-pyridin-3-yloxy)-1,2,3,4-tetrahydro-isoquinoline; 2-Methyl-4-(4-methylsulfanyl-phenyl)-7-(4-piperidin-1-ylmethyl-phenoxy)-1,2,3,4-tetrahydro-isoquinoline; 2-Methyl-4-(4-methylsulfanyl-phenyl)-7-(5-morpholin-4-ylmethyl-pyridin-2-yloxy)-1,2,3,4-tetrahydro-isoquinoline; 2-Methyl-4-(4-methylsulfanyl-phenyl)-7-(4-morpholin-4-ylmethyl-thiazol-2-yloxy)-1,2,3,4-tetrahydro-isoquinoline; 7-[5-(4-Fluoro-piperidin-1-ylmethyl)-pyridin-2-yloxy]-2-methyl-4-(4-methylsulfanyl-phenyl)-1,2,3,4-tetrahydroisoquinoline; 2-Methyl-4-(4-methylsulfanyl-phenyl)-7-(5-piperidin-1-ylmethyl-thiazol-2-yloxy)-1,2,3,4-tetrahydro-isoquinoline;

and pharmaceutically acceptable salts thereof.

13. A compound or pharmaceutically acceptable salt according to claim 1.

14. A pharmaceutical composition comprising:

(a) an effective amount of a compound of Formula (I):

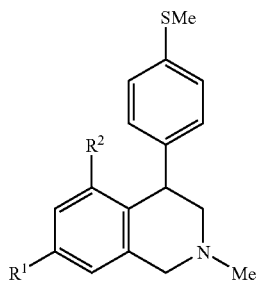

(I)

wherein one of $R^1$ and $R^2$ is H and the other is

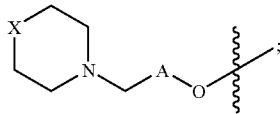

where A is phenyl, pyridyl, or thiazolyl; and

X is $CH_2$, O, or CHF;

or a pharmaceutically acceptable salt, or a pharmaceutically acceptable prodrug thereof; and (b) a pharmaceutically acceptable excipient.

15. A pharmaceutical composition according to claim 14, further comprising: an active ingredient selected from the group consisting of $H_1$ receptor antagonists, $H_2$ receptor antagonists, $H_3$ receptor antagonists, serotonin-norepinephrine reuptake inhibitors, selective serotonin reuptake inhibitors, noradrenergic reuptake inhibitors, non-selective serotonin re-uptake inhibitors, acetylcholinesterase inhibitors, modafinil, and topiramate.

* * * * *